United States Patent
Green et al.

(10) Patent No.: US 7,901,933 B2
(45) Date of Patent: Mar. 8, 2011

(54) METHODS OF PROCESSING A BIOLOGICAL GROWTH PLATE IN A BIOLOGICAL GROWTH PLATE SCANNER

(75) Inventors: Kevin R. Green, Maplewood, MN (US); Doyle T. Potter, White Bear Lake, MN (US); Andrew D. Dubner, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 12/877,254

(22) Filed: Sep. 8, 2010

(65) Prior Publication Data
US 2010/0330610 A1    Dec. 30, 2010

Related U.S. Application Data

(60) Continuation of application No. 11/934,175, filed on Nov. 2, 2007, which is a division of application No. 10/306,579, filed on Nov. 27, 2002, now Pat. No. 7,298,885.

(51) Int. Cl.
C12M 1/34    (2006.01)
C12M 3/00    (2006.01)
C12M 1/22    (2006.01)

(52) U.S. Cl. .................... 435/287.9; 435/305.1
(58) Field of Classification Search ............ 435/287.9, 435/305.1
See application file for complete search history.

(56) References Cited

U.S. PATENT DOCUMENTS

| | | |
|---|---|---|
| 3,493,772 A | 2/1970 | Daughters et al. |
| 3,745,090 A | 7/1973 | Chappelle et al. ............ 195/103 |
| 3,811,036 A | 5/1974 | Perry |
| 3,962,040 A | 6/1976 | Campbell et al. |
| 4,118,280 A | 10/1978 | Charles et al. |
| 4,146,775 A | 3/1979 | Kirchner et al. ............ 219/295 |
| 4,160,601 A | 7/1979 | Jacobs |
| 4,353,988 A | 10/1982 | Couse et al. |
| 4,563,096 A * | 1/1986 | Chidlow et al. ............ 356/440 |
| 4,591,567 A | 5/1986 | Britten et al. |
| 4,637,053 A | 1/1987 | Schalkowsky |
| 4,720,463 A | 1/1988 | Farber et al. |
| 4,724,215 A | 2/1988 | Farber et al. |

(Continued)

FOREIGN PATENT DOCUMENTS

DE    19819144    4/1998

(Continued)

OTHER PUBLICATIONS

Kalasinsky, Kathryn S. et al.; "Raman Chemical Imaging Spectroscopy Reagentless Detection and Identification of Pathogens: Signature Development and Evaluation"; Analytical Chemistry; 2007; 79 (7) pp. 2658-2673.

(Continued)

Primary Examiner — Walter D Griffin
Assistant Examiner — Lydia Edwards

(57) ABSTRACT

Methods are provided to process a biological growth plate using a biological growth plate scanner. The scanner includes an imaging device, a processor, and an image processing profile memory. The scanner scans a plate type indicator associated with the biological growth plate. In some embodiments, the processor uses the plate type indicator to verify the suitability of the biological growth plate for use in the scanner. In some embodiments, the processor uses the plate type indicator to unlock the scanner for operation.

4 Claims, 13 Drawing Sheets

U.S. PATENT DOCUMENTS

| | | | |
|---|---|---|---|
| 4,817,785 A | 4/1989 | Farber et al. | |
| 4,856,073 A | 8/1989 | Farber et al. | |
| 5,117,467 A | 5/1992 | Misaki et al. | |
| 5,202,010 A | 4/1993 | Guzman | 204/299 |
| 5,270,173 A | 12/1993 | Yonemori et al. | 435/29 |
| 5,290,701 A | 3/1994 | Wilkins | |
| 5,329,686 A | 7/1994 | Kildal et al. | |
| 5,364,766 A | 11/1994 | Mach et al. | |
| 5,366,873 A | 11/1994 | Eden et al. | |
| 5,372,485 A | 12/1994 | Sumser et al. | |
| 5,372,936 A | 12/1994 | Fraatz et al. | |
| 5,375,043 A | 12/1994 | Tokunaga | |
| 5,403,722 A | 4/1995 | Floeder et al. | |
| 5,428,690 A * | 6/1995 | Bacus et al. | 382/128 |
| 5,448,652 A | 9/1995 | Vaidyanathan et al. | |
| 5,510,246 A | 4/1996 | Morgan | |
| 5,539,517 A | 7/1996 | Cabib et al. | |
| 5,573,950 A * | 11/1996 | Graessle et al. | 435/287.3 |
| 5,591,974 A | 1/1997 | Troyer et al. | 250/336 |
| 5,671,290 A | 9/1997 | Vaidyanathan | |
| 5,694,478 A | 12/1997 | Braier et al. | |
| 5,721,435 A | 2/1998 | Troll | |
| 5,723,308 A | 3/1998 | Mach et al. | |
| 5,744,322 A | 4/1998 | Krejcarek et al. | |
| 5,747,333 A | 5/1998 | Jungmann-Campello et al. | |
| 5,781,311 A | 7/1998 | Inoue et al. | |
| 5,787,189 A | 7/1998 | Lee et al. | |
| 5,817,475 A | 10/1998 | Gibbs et al. | |
| 5,995,645 A | 11/1999 | Soenksen et al. | |
| 6,002,789 A | 12/1999 | Olsztyn et al. | |
| 6,058,209 A | 5/2000 | Vaidyanathan et al. | 382/203 |
| 6,096,272 A | 8/2000 | Clark et al. | |
| 6,107,054 A * | 8/2000 | Gibbs | 435/32 |
| 6,238,879 B1 * | 5/2001 | Gibbs | 435/32 |
| 6,243,486 B1 | 6/2001 | Weiss | |
| 6,271,022 B1 | 8/2001 | Bochner | |
| 6,319,668 B1 * | 11/2001 | Nova et al. | 506/28 |
| 6,372,485 B1 | 4/2002 | Clark et al. | |
| 6,381,353 B1 | 4/2002 | Weiss | |
| 6,418,180 B1 | 7/2002 | Weiss | |
| 6,459,994 B1 * | 10/2002 | Parekh et al. | 702/19 |
| 6,485,979 B1 * | 11/2002 | Kippenhan et al. | 436/1 |
| 6,488,890 B1 | 12/2002 | Kirckof | |
| 6,642,953 B1 | 11/2003 | Nieto Velasco et al. | |
| 6,673,315 B2 * | 1/2004 | Sheridan et al. | 422/50 |
| 6,690,470 B1 | 2/2004 | Baer et al. | |
| 6,711,283 B1 | 3/2004 | Soenksen | |
| 6,737,266 B1 * | 5/2004 | Wicks et al. | 435/288.2 |
| 6,999,607 B2 * | 2/2006 | Kiros et al. | 382/128 |
| 7,057,721 B2 | 6/2006 | Gardiner, Jr. et al. | 356/301 |
| 7,298,885 B2 | 11/2007 | Green et al. | 382/133 |
| 7,298,886 B2 | 11/2007 | Plumb et al. | 382/133 |
| 7,496,225 B2 | 2/2009 | Graessle et al. | 382/133 |
| 2001/0031502 A1 | 10/2001 | Watson, Jr. et al. | |
| 2002/0025082 A1 * | 2/2002 | Kaushikkar et al. | 382/294 |
| 2002/0064867 A1 | 5/2002 | Clark et al. | |
| 2002/0137091 A1 | 9/2002 | Luttermann et al. | |
| 2002/0167161 A1 * | 11/2002 | Butland | 283/72 |
| 2002/0191825 A1 * | 12/2002 | Parekh et al. | 382/128 |
| 2004/0101189 A1 | 5/2004 | Green et al. | |
| 2004/0101951 A1 | 5/2004 | Vent et al. | |
| 2004/0101952 A1 | 5/2004 | Vent et al. | |
| 2004/0101954 A1 | 5/2004 | Graessle et al. | |
| 2004/0102903 A1 | 5/2004 | Graessle et al. | |
| 2005/0053265 A1 | 3/2005 | Graessle et al. | 382/128 |
| 2005/0053266 A1 | 3/2005 | Plumb et al. | 382/128 |
| 2005/0095665 A1 | 5/2005 | Williams et al. | 435/34 |
| 2005/0222778 A1 | 10/2005 | Levinson et al. | 702/19 |
| 2006/0263258 A1 | 11/2006 | Harris et al. | 422/99 |
| 2008/0003562 A1 | 1/2008 | Plumb et al. | 435/3 |

FOREIGN PATENT DOCUMENTS

| | | |
|---|---|---|
| EP | 0 008 826 A2 | 3/1980 |
| EP | 0 088 601 A1 | 9/1983 |
| EP | 0 301 600 | 1/1989 |
| EP | 0 397 256 A2 | 11/1990 |
| EP | 0 397 256 A3 | 11/1990 |
| EP | 0 429 030 A2 | 5/1991 |
| EP | 0 429 030 A3 | 5/1991 |
| EP | 0 193 385 B1 | 7/1992 |
| EP | 0 547 709 A2 | 6/1993 |
| EP | 0 547 709 A3 | 6/1993 |
| EP | 0 819 930 A2 | 1/1998 |
| EP | 0 895 086 A2 | 2/1999 |
| EP | 1 074 610 | 2/2001 |
| GB | 2 249 829 A | 5/1992 |
| JP | 60-83597 | 5/1985 |
| JP | 62-215383 | 9/1987 |
| JP | 5-249105 | 9/1993 |
| JP | 6-98220 | 4/1994 |
| JP | 6-109545 | 4/1994 |
| JP | 7-275200 | 10/1995 |
| JP | 10-24283 | 1/1998 |
| JP | 10-500302 | 1/1998 |
| JP | 2000-270840 | 10/2000 |
| JP | 2001-242082 | 7/2001 |
| JP | 2002-538440 | 11/2002 |
| WO | WO 91/06911 | 5/1991 |
| WO | WO 92/12233 | 7/1992 |
| WO | WO 94/01528 | 1/1994 |
| WO | WO 94/26926 | 11/1994 |
| WO | WO 95/16768 | 6/1995 |
| WO | WO95/31732 | 11/1995 |
| WO | WO 96/18721 | 6/1996 |
| WO | WO 98/53301 | 11/1998 |
| WO | WO 98/59314 | 12/1998 |
| WO | WO 99/28436 | 6/1999 |
| WO | WO 00/32807 | 6/2000 |
| WO | WO 00/49129 | 8/2000 |
| WO | WO 00/49130 | 8/2000 |
| WO | WO 00/51058 | 8/2000 |
| WO | WO 00/65094 | 11/2000 |
| WO | WO 01/04828 A1 | 1/2001 |
| WO | WO 01/09371 | 2/2001 |
| WO | WO 01/83673 A2 | 11/2001 |
| WO | WO 02/90966 | 1/2002 |
| WO | WO02/37938 | 5/2002 |
| WO | WO02/38724 | 5/2002 |
| WO | WO 02/46354 | 6/2002 |
| WO | WO 02/066961 A1 | 8/2002 |
| WO | WO 03/014400 | 2/2003 |
| WO | WO 03/038413 | 5/2003 |

OTHER PUBLICATIONS

Decision on Appeal dated Dec. 2, 2008 in U.S. Appl. No. 10/306,663, filed Nov. 27, 2002 (18 pgs.).

Corkidi et al.; "*COVASIAM: an Image Analysis Method That Allows Detection of Confluent Microbial Colonies and Colonies of Various Sizes for Automated Counting*", Applied and Environmental Microbiology, vol. 64, No. 4, Apr. 1998, pp. 1400-1404.

Gilchrist et al., "Spiral Plate Method for Bacterial Determination", Applied Microbiology, Feb. 1973, vol. 25, No. 2, pp. 244-252.

Ilya et al; "Streamlined Yeast Colorimetric Reporter Activity Assays Using Scanners and Plate Readers", BioTechniques, vol. 29, No. 2, Aug. 2000.

K. M. Wright et al.; "Determination of Mean Growth Parameters of Bacterial Colonies Immobilized in Gelatin Gel Using a Laser Gel-cassette Scanner", International journal of Food Microbiology, 2000, pp. 75-89.

Product brochure entitled "Efficient Batch Handling" by ProtoZONE, Synbiosis, a division of Synoptic Ltd., Cambridge, UK (4 pgs.).

Product brochure entitled "Petrifilm™ Information Management System—Reduce Operational Costs and Increase Productivity"; 3M Microbiology Products; 1999; 70-2009-1996-0; (3 pgs.).

Product brochure entitled "Powerful data handling for GLP conformance"by ProtoCOL, Synbiosis, a division of Synoptic Ltd, Cambridge, UK (4 pgs.).

* cited by examiner

METHODS OF PROCESSING A BIOLOGICAL GROWTH PLATE IN A BIOLOGICAL GROWTH PLATE SCANNER

CROSS REFERENCE TO RELATED APPLICATIONS

This application is a continuation of U.S. patent application Ser. No. 11/934,175, filed on Nov. 2, 2007; which was a divisional application of U.S. patent application Ser. No. 10/306,579, filed Nov. 27, 2002, now U.S. Pat. No. 7,298,885; the disclosures of which are incorporated herein by reference in their entirety.

FIELD

The invention relates to techniques for analysis of biological growth media to analyze bacteria or other biological agents in food samples, laboratory samples, and the like.

BACKGROUND

Biological safety is a paramount concern in modern society. Testing for biological contamination in foods or other materials has become an important, and sometimes mandatory requirement for developers and distributors of food products. Biological testing is also used to identify bacteria or other agents in laboratory samples such as blood samples taken from medical patients, laboratory samples developed for experimental purposes, and other types of biological samples. Various techniques and devices can be utilized to improve biological testing and to streamline and standardize the biological testing process.

In particular, a wide variety of biological growth media have been developed. As one example, biological growth media in the form of growth plates have been developed by 3M Company (hereafter "3M") of St. Paul, Minn. Biological growth plates are sold by 3M under the trade name PETRIFILM plates. Biological growth plates can be utilized to facilitate the rapid growth and detection or enumeration of bacteria or other biological agents commonly associated with food contamination, including, for example, aerobic bacteria, *E. coli*, coliform, enterobacteriaceae, yeast, mold, *Staphylococcus aureus, Listeria, Campylobacter*, and the like. The use of PETRIFILM plates, or other growth media, can simplify bacterial testing of food samples.

Biological growth media can be used to identify the presence of bacteria so that corrective measures can be performed (in the case of food testing) or proper diagnosis can be made (in the case of medical use). In other applications, biological growth media may be used to rapidly grow bacteria or other biological agents in laboratory samples, e.g., for experimental purposes.

Biological scanners refer to devices used to read or count bacterial colonies, or the amount of a particular biological agent on a biological growth medium. For example, a food sample or laboratory sample can be placed on a biological growth medium, and then the medium can be inserted into an incubation chamber. After incubation, the biological growth medium can be placed into the biological scanner for automated detection and enumeration of bacterial growth. In other words, biological scanners automate the detection and enumeration of bacteria or other biological agents on a biological growth medium, and thereby improve the biological testing process by reducing human error.

SUMMARY

In general, the invention is directed to a biological scanner that automates selection of image processing profiles to scan and analyze different types of biological growth plates. The scanner automatically identifies the type of plate to be scanned, and then selects one of the image processing profiles appropriate for the identified plate type.

The scanner may identify the plate type by reference to a variety of machine-readable indicators, such as optically or magnetically readable marks, carried on the plate. Accordingly, the invention also is directed to biological growth plates carrying particular indicators that permit plate type identification for selection of image processing profiles.

The plates may be scanned in order to read or count different types of bacterial colonies, or the amount of a particular biological agent on the biological growth plate. In operation, the scanner identifies the plate type, e.g., upon presentation of the biological growth plate to the scanner. The scanner then processes the image according to an image processing profile associated with the identified plate type.

The image processing profile may specify particular image capture conditions, such as illumination intensities, durations, and colors, for capturing images of particular plate types. The image capture conditions also may include camera gain, resolution, aperture, and exposure time. In addition, the image processing profile may specify particular image analysis criteria, such as color, shape, size and proximity criteria, for detecting or enumerating different types of bacterial colonies within a captured image. Thus, the scanner may apply different image capture conditions, different image analysis criteria, or both in processing an image of the biological growth plate.

In operation, upon plate type identification, the biological scanner may select a corresponding image processing profile. The biological scanner may illuminate the biological growth plate using image capture conditions specified by the image processing profile and capture one or more images of the plate. The biological scanner then may perform an analysis of the captured image using image analysis criteria specified by the image processing profile. In this manner, the biological scanner automates the scanning and analysis of different types of biological growth plates.

In one embodiment, the invention provides a device comprising a memory that stores a set of image processing profiles, and an image processing device that selects one of the image processing profiles based on a plate type associated with a biological growth plate.

In another embodiment, the invention provides a method comprising detecting a plate type associated with a biological growth plate, selecting one of a plurality of image processing profiles based on the detected plate type, and processing an image of the biological growth plate according to the selected image processing profile.

In an additional embodiment, the invention provides a computer-readable medium comprising instructions for causing a processor to select one of a plurality of image processing profiles based on a detected plate type for a biological growth plate, and control an image processing device to process an image of the biological growth plate according to the selected image processing profile.

In a further embodiment, the invention provides a biological growth plate comprising a plate surface to support growth of a biological agent, and a machine-readable plate type indicator that identifies a type of the biological growth plate.

In another embodiment, the invention provides a system comprising a biological growth plate including a machine-readable plate type indicator that identifies a plate type of the biological growth plate, and an imaging device to capture an image of the biological growth plate and process the image according to one of a plurality of image processing profiles selected based on the plate type indicator.

The invention can provide a number of advantages. For example, automated image processing profile selection can provide a convenient and accurate technique for selecting the appropriate image processing profile. Automated image processing profile selection can promote the accuracy of bacterial colony counts and other analytical procedures, enhancing quality assurance. In particular, appropriate image capture conditions and image analysis criteria can be automatically selected and applied for each plate type. Automatic image processing profile selection can avoid the need for a technician to visually identify and manually enter the plate type, and thereby eliminate plate identification errors sometimes associated with human intervention. Analytical accuracy can be a critical health concern, particularly when testing food samples. In addition, automated image processing profile selection can promote efficiency and convenience, and improve workflow for laboratory technicians. A biological growth plate carrying a machine-readable plate type indicator that permits automated plate type identification by a biological scanner can contribute to the foregoing advantages.

Additional details of these and other embodiments are set forth in the accompanying drawings and the description below. Other features, objects and advantages will become apparent from the description and drawings, and from the claims.

DETAILED DESCRIPTION

Figure 1:
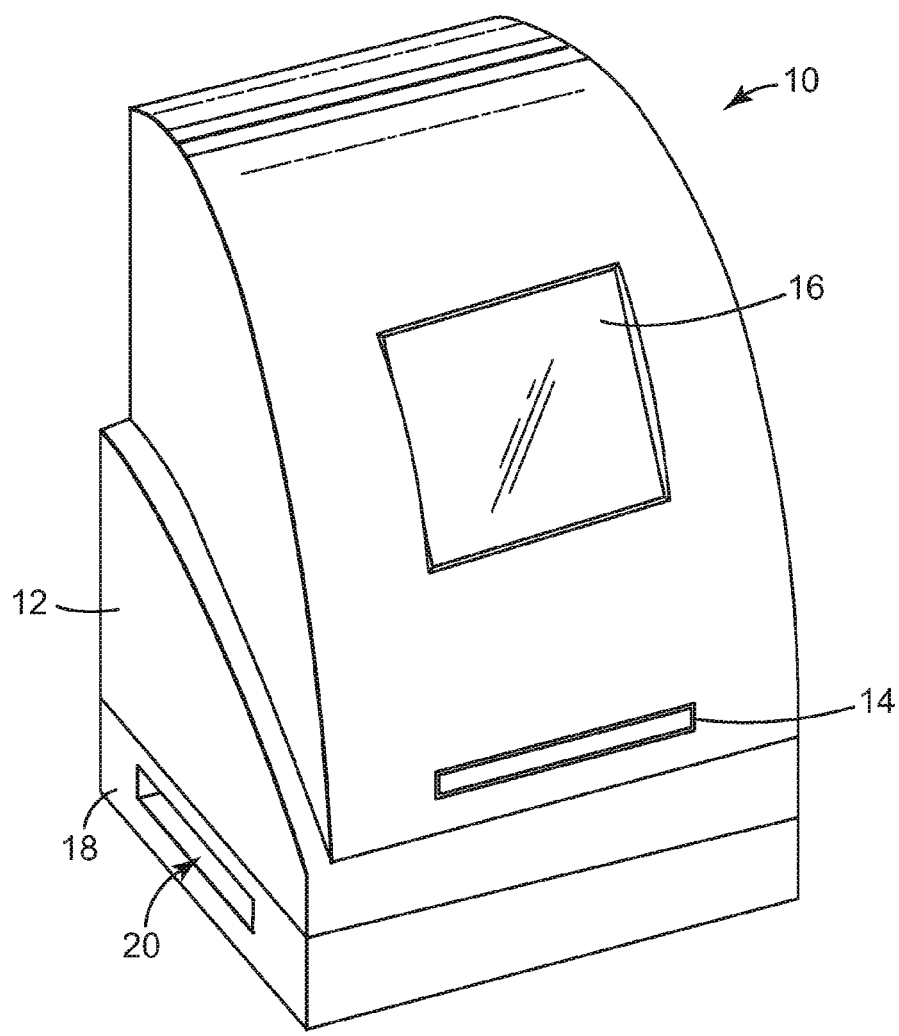
FIG. 1 is a perspective view of an exemplary biological scanner.

The invention is directed to a biological scanner for biological growth plates. A biological growth plate can be presented to the biological scanner, which then generates an image of the plate and performs an analysis of the image to detect biological growth. For example, the scanner may count or otherwise quantify an amount of biological agents that appear in the image, such as a number of bacteria colonies. In this manner, the biological scanner automates the analysis of biological growth plates, thereby improving such analysis and reducing the possibility of human error.

A biological scanner, in accordance with the invention, also automates selection of image processing profiles to scan different types of biological growth plates and analyze plate images. The scanner automatically identifies the type of plate to be scanned by the scanner, and then selects one of the image processing profiles appropriate for the identified plate type. The image processing profiles may specify image capture conditions, image analysis criteria or a combination of both for different types of biological growth plates. For example, the image processing profile may specify illumination intensities, durations, and colors for illumination of particular plate types for image capture. The image capture conditions also may include camera gain, resolution, aperture, and exposure time. In terms of image analysis criteria, the image processing profiles may specify different color, shape, size and proximity criteria in counting different types of bacterial colonies within a captured image to promote accuracy in the analytical result, e.g., a count. Hence, the image processing profiles may pertain both to image capture and analysis. Accuracy is critical in both food and laboratory sample test environments. For food safety, in particular, accurate results permit verification of sanitation at critical control points throughout the food processing operation, including line production, equipment and environmental testing.

The scanner may identify the plate type by reference to a variety of machine-readable plate type indicators, such as optically or magnetically readable marks, carried on the plate. Accordingly, the invention also contemplates biological growth plates carrying a particular indicator that permits plate type identification. In addition, the invention may eliminate or reduce reliance on human judgment in making plate type identifications, thereby reducing the potential for human error and resulting inaccuracy in colony counts or other analyses.

The invention may be useful with a variety of biological growth plates. For example, the invention may be useful with different plate-like devices for growing biological agents to enable detection or enumeration of the agents, such as thin-film culture plate devices, Petri dish culture plate devices, and the like. Therefore, the term "biological growth plate" will be used broadly herein to refer to a medium suitable for growth of biological agents to permit detection and enumeration of the agents by a scanner. In some embodiments, the biological growth plate can be housed in a cassette that supports multiple plates, e.g., as described in U.S. Pat. No. 5,573,950 to Graessle et al.

FIG. 1 is a perspective view of an exemplary biological scanner 10. As shown in FIG. 1, biological scanner 10 includes a scanner unit 12 having a drawer 14 that receives a biological growth plate (not shown in FIG. 1). Drawer 14 moves the biological growth plate into biological scanner 10 for scanning and analysis. Scanner 10 may incorporate features that permit automated plate type identification, and automated selection of image processing profiles based on plate type, in accordance with the invention.

Biological scanner 10 also may include a display screen 16 to display the progress or results of analysis of the biological growth plate to a user. Alternatively or additionally, display screen may present to a user an image of the growth plate scanned by biological scanner 10. The displayed image may be optically magnified or digitally scaled upward. A mounting platform 18 defines an ejection slot 20 through which the growth plate can be ejected following image capture by biological scanner 10. Accordingly, biological scanner 10 may have a two-part design in which scanner unit 12 is mounted on mounting platform 18. The two-part design is depicted in FIG. 1 for purposes of example, and is not intended to be required by or limiting of the inventions described herein.

Scanner unit 12 houses an imaging device for scanning the biological growth plate and generating an image. The imaging device may take the form of a line scanner or an area scanner, which ordinarily will be provided in combination with an illumination system to provide front and/or back illumination of the biological growth plate. In addition, scanner unit 12 may house processing hardware that performs analysis of the scanned image, e.g., in order to determine the number or amount of biological agents in the growth plate. For example, upon presentation of the biological growth plate via drawer 14, the plate may be positioned adjacent an optical platen for scanning.

When the drawer is subsequently opened, the growth plate may drop downward into the mounting platform 18 for ejection via ejection slot 20. To that end, mounting platform 18 may house a conveyor that ejects the growth plate from biological scanner 10 via ejection slot 20. After a biological growth plate is inserted into drawer 14, moved into scanner unit 12, and scanned, the biological growth plate drops downward into mounting platform 18, where a horizontal conveyor, such as a moving belt, ejects the medium via slot 20.

Figure 2:
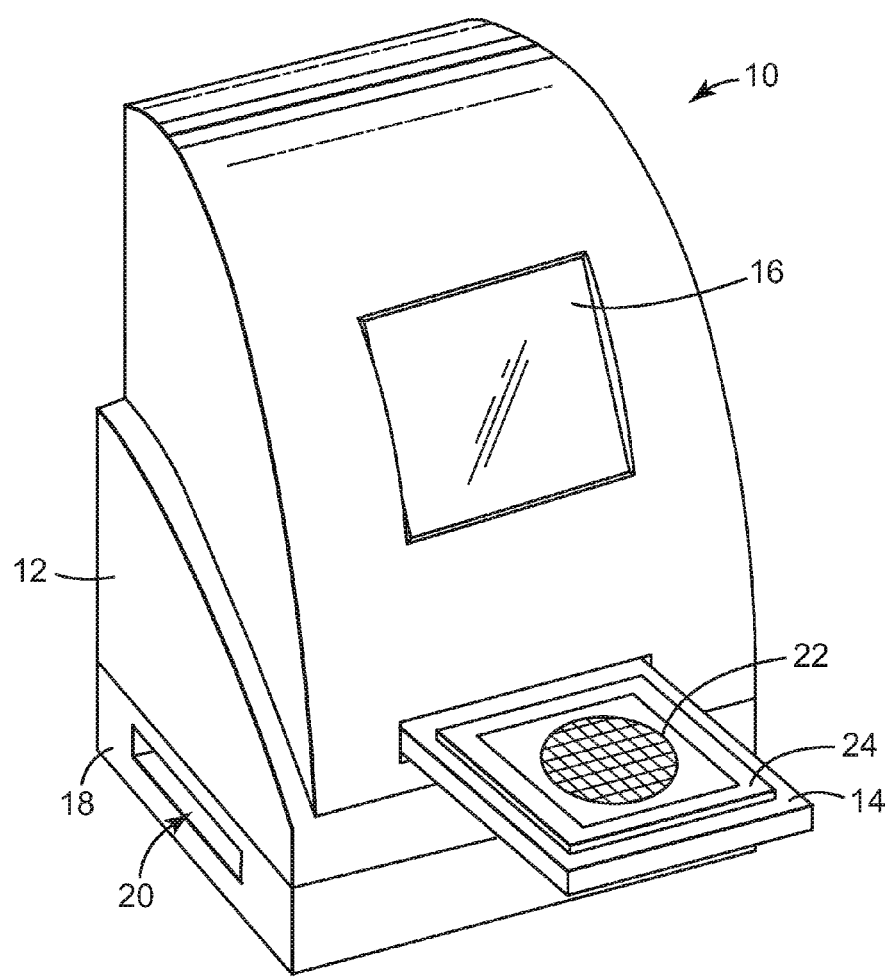
FIG. 2 is another perspective view of an exemplary biological scanner.

FIG. 2 is another perspective view of biological scanner 10. As shown in FIG. 2, drawer 14 extends outward from biological scanner 10 to receive a biological growth plate 22. As illustrated, a biological growth plate 22 may be placed on a platform 24 provided within drawer 14. In some embodiments, platform 24 may include positioning actuators such as cam levers to elevate the platform for precise positioning of growth plate 22 within biological scanner 10. Upon placement of biological growth plate 22 on platform 24, drawer 14 retracts into scanner unit 12 to place the biological growth plate in a scanning position, i.e., a position at which the biological growth medium is optically scanned.

Figure 3:
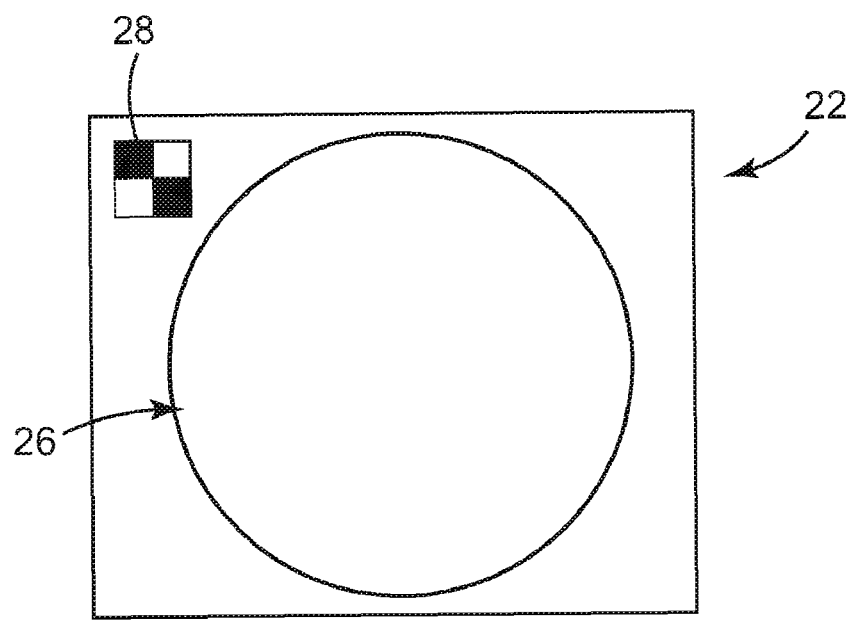
FIGS. 3 and 4 are top views of an exemplary growth plate bearing an indicator pattern for image processing profile selection.
Figure 4:
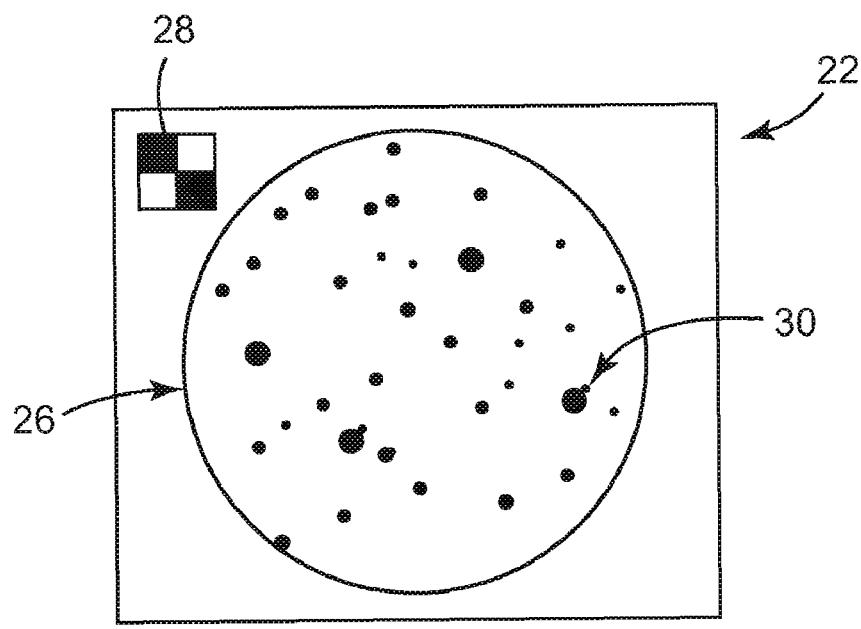

FIGS. 3 and 4 are top views of an exemplary biological growth plate 22. By way of example, a suitable growth plate 22 may comprise biological growth plates sold by 3M under the trade name PETRIFILM plates. Alternatively, biological growth plate 22 may comprise other biological growth media for growing particular bacteria or other biological agents. In accordance with the invention, biological growth plate 22 carries plate type indicator 28 to facilitate automated identification of the type of biological media associated with the growth plate.

Plate type indicator 28 presents an encoded pattern that is machine-readable. In the example of FIGS. 3 and 4, plate type indicator 28 takes the form of an optically readable pattern. In particular, FIGS. 3 and 4 depict a four-square pattern of light and dark quadrants formed in a corner margin of biological growth plate 22. In other words, plate type indicator 28 defines a two-dimensional grid of cells modulated between black and white to form an encoded pattern. A wide variety of optical patterns such as characters, bar codes, two-dimensional bar codes, optical gratings, holograms, phosphorous inks and the like are conceivable.

In addition, in some embodiments, plate type indicator 28 may take the form of patterns that are readable by magnetic or radio frequency techniques. Alternatively, plate type indicator 28 may take the form of apertures, slots, surface contours, or the like that are readable by optical or mechanical techniques. In each case, plate type indicator 28 carries information sufficient to enable automated identification of the type of biological growth plate 22 by biological scanner 10. Plate type indicator 28 will be described in greater detail below.

Biological growth plates may facilitate the rapid growth and detection and enumeration of bacteria or other biological agents including, for example, aerobic bacteria, *E. coli*, coliform, enterobacteriaceae, yeast, mold, *Staphylococcus aureus*, *listeria*, and *campylobacter*, and the like. The use of PETRIFILM plates, or other growth media, can simplify bacterial testing of food samples. Moreover, as outlined herein, biological scanner 10 can further simplify such testing by providing automated plate type detection, and automated selection of image processing profiles based on the detected plate type to illuminate and/or analyze biological growth plate 22, e.g., by counting bacterial colonies on an image of the plate.

As shown in FIG. 3, biological growth plate 22 defines a growth area 26. A determination of whether a given sample being tested in plate 22 is acceptable, in terms of bacterial colony counts, may depend on the number of bacterial colonies per unit area. Accordingly, scanner 10 may quantify the amount of bacterial colonies per unit area on plate 22, and may compare the amount, or "count," to a threshold. The surface of biological growth plate 22 may contain one or more growth enhancing agents designed to facilitate the rapid growth of one or more types of bacteria or other biological agents.

After placing a sample of the material being tested, typically in liquid form, on the surface of biological growth plate 22 within growth area 26, plate 22 can be inserted into an incubation chamber (not shown). In the incubation chamber, bacterial colonies or other biological agents being grown by growth plate 22 manifest themselves, as shown in biological growth plate 22 of FIG. 4. The colonies, represented by various dots 30 on biological growth plate 22 in FIG. 4, may appear in different colors on plate 22, facilitating automated detection and enumeration of bacterial colonies by scanner 10.

FIGS. 5A-5D are diagrams illustrating exemplary plate type indicator 28 carried by a biological growth plate 22 for image processing profile selection. Again, plate type indicator 28 may take the form of patterns, marks, apertures, surface contours and the like, which permit optical or mechanical readability. For example, different optical patterns can be read by optical decoders, bar code scanners, optical character recognition (OCR) processors or the like. In the case of apertures or contours, mechanical styli may interact with the apertures or contours to detect different patterns and produce an electrical signal. Alternatively, plate type indicator 28 may be magnetically encoded stripes or markers or carry radio frequency identifications to permit magnetic or radio frequency readability.

Optically readable patterns may be formed by printing or deposition of ink on the surface of biological growth plate 22, e.g., outside of growth area 26. Apertures or surface contour patterns can be formed in biological growth plate 22 by punches, stamps, embossers, die cutters and the like. A magnetic stripe or radio frequency identification may be affixed to the surface of biological growth plate 22, e.g., by adhesive or lamination techniques. In addition, a magnetic or radio frequency indicator need not be carried on the surface of biological growth plate 22, but may be interposed between layers of the growth plate in the event the growth plate has a multi-layer structure. In each case, the various plate type indicators 28 may be formed at the factory to identify the type of biological growth plate 22.

In addition, if desired, plate type indicator 28 may further include information that identifies a particular manufacturer, lot number, expiration date, security authorization, and the like. Such additional items of information may be important in verifying quality and suitability of biological growth plate 22 for used in biological scanner 10. For example, one or more manufacturers may be specifically validated, e.g., on the basis of plate production quality and plate performance criteria, to provide biological growth plates 22 for use in biological scanner 10. In this case, biological scanner 10 may be configured to reject biological growth plates 22 that, according to plate type indicator 28, are not associated with validated manufacturers.

In addition, plate type indicator 28 may carry security information, such as serial number codes or the like, that serve to authenticate biological growth plate 22 and prevent fraudulent introduction of unauthorized growth plates, e.g., to thwart the food inspection or laboratory analysis process. Although such information may be integrated and encoded within biological growth plate 22, it may alternatively be encoded within separate indicator patterns carried by the growth plate. Accordingly, biological growth plate 22 may carry one or more indicator patterns, in addition to plate type indicator 28, which serve different security and quality assurance purposes.

To enhance security, plate type indicator 28, as well as any other indicators that may be carried by biological growth plate 22, may benefit from a variety of security mechanisms. For example, in some embodiments, a printed plated type indicator 28 may be printed with a particular phosphorous ink so that it can be conspicuously identified according to the wavelength of light emitted by the indicator when it is scanned. In addition, plate type indicators 28 may take the form of more complex patterns that carry encryption keys to unlock biological scanner 10 for operation. In this case, processor 34 in biological scanner 10 (FIG. 6) would perform decryption of the pattern in order to proceed with image processing.

Figure 5A:
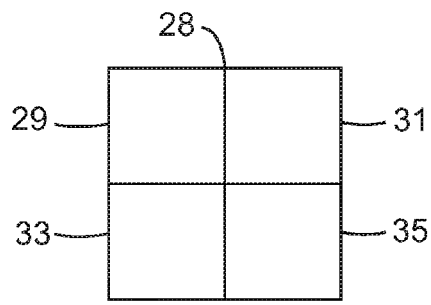
FIGS. 5A-5D are diagrams illustrating exemplary plate type indicator patterns carried by a biological growth plate for image processing profile selection.
Figure 5B:
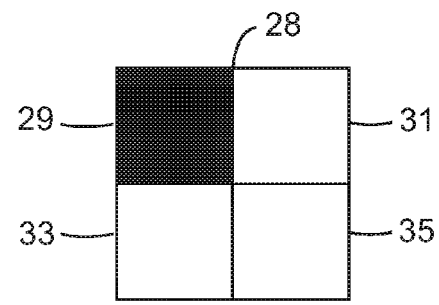
Figure 5C:
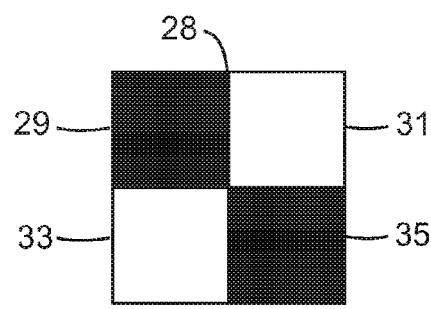
Figure 5D:
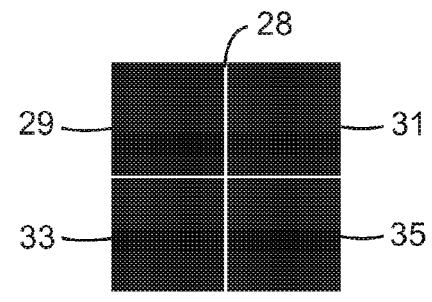

In the example of FIGS. 5A-5D, plate type indicator 28 takes the form of a four-square pattern having four quadrants 29, 31, 33, 35 that can be either dark or light, permitting ready optical processing. In FIG. 5A, plate type indicator 28 has four light quadrants, and may identify a first type of biological growth plate 22. In FIGS. 5B, 5C and 5D, plate type indicator 28 include one black quadrant, two black quadrants, and four black quadrants, respectively. Selection of the number and position of the black quadrants permits up to sixteen ($2^4$) different encoded patterns to be formed and, accordingly, up to sixteen different plate types to be identified by machine-readable plate type indicator 28. As examples, different encoded patterns could represent Aerobic Count, Coliform, E. Coli, Staphylococcus aureus, Yeast and Mold, and other plate type designations.

Although the form of plate type indicator 28 may be subject to wide variation, the 4-square pattern shown in FIGS. 5A-5D provides one type of pattern that is relatively simple and easy to identify using optical pattern recognition techniques, i.e., machine vision. As will be described, plate type indicator 28 may be scanned by a dedicated optical code reader, such as a bar code reader or custom reader. In this case, plate type indicator 28 can be scanned prior to or in parallel with scanning of biological growth plate 22, but before processing of the growth plate image. Alternatively, plate type indicator 28 may be captured in a scanned image of biological growth plate 22, and then extracted for image processing to identify the plate type. In this case, the plate type can be identified before further image processing of the scanned growth plate image.

Figure 6:
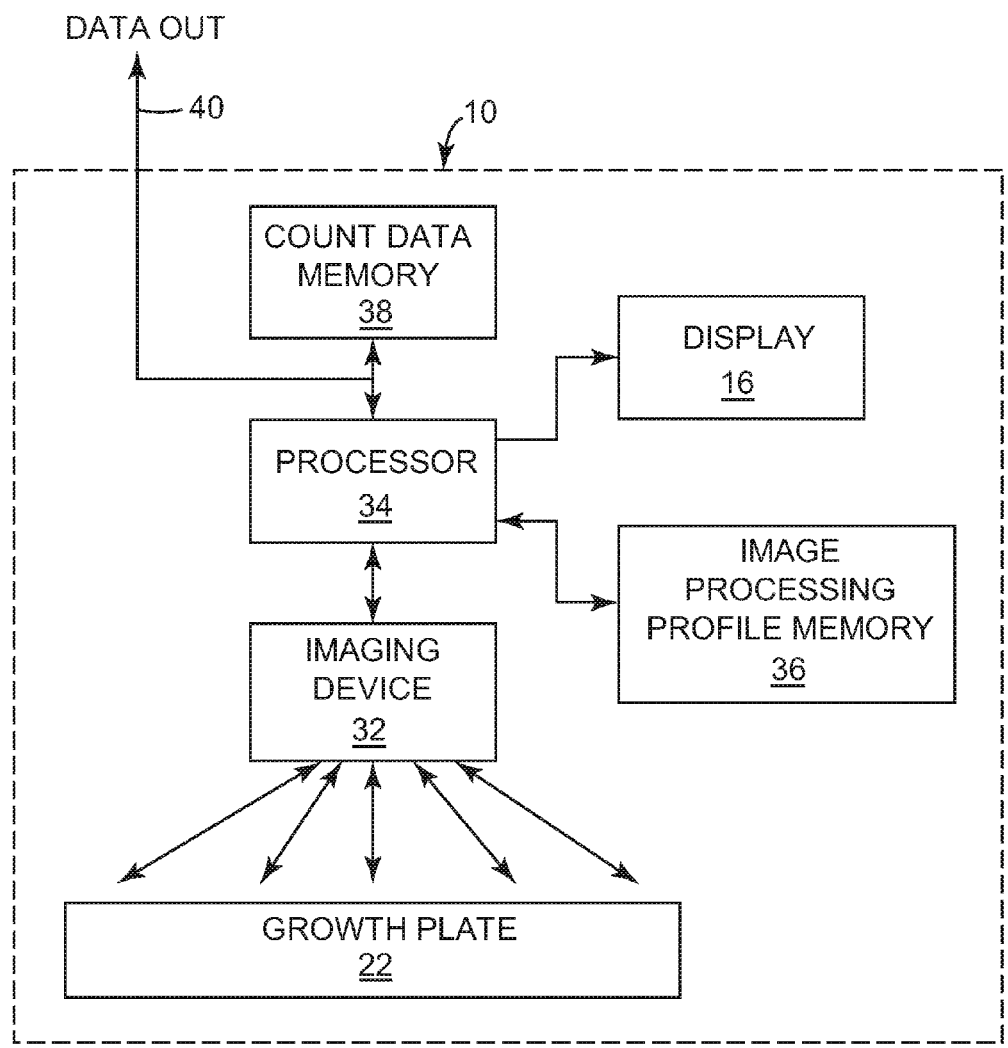
FIG. 6 is a block diagram illustrating a biological scanner configured for automated image processing profile selection.

FIG. 6 is a block diagram illustrating internal operation of biological scanner 10. As illustrated in FIG. 6, a biological growth plate 22 is positioned within biological scanner 10 on a platform (not shown in FIG. 6). The platform places biological growth plate 22 at a desired focal plane of an imaging device 32. Imaging device 32 may include illumination hardware for top and back illumination of growth plate 22, as well as a line or area scanner that captures an image of the surface of growth plate 22. Imaging device 32 may apply standard image capture conditions, or a user may specify image capture conditions. Alternatively, as will be described below, scanner 10 may automatically control image capture conditions based on an image processing profile that corresponds to a plate type.

In some embodiments, for example, imaging device 32 may take the form of a two-dimensional camera, although line scanners can be used in configurations in which either the canner or biological growth plate 22 is translated relative to the other. In general, image device 32 captures an image of biological growth plate 22, or at least a growth region within the biological growth plate. A processor 34 controls the operation of imaging device 32. In operation, processor 34 controls imaging device 32 to capture an image of biological growth plate 22. Processor 34 receives image data representing the scanned image from imaging device 32, and extracts or segregates a portion of the image to isolate plate type indicator 28.

Using machine vision techniques, processor 34 analyzes plate type indicator 28 to identify a plate type associated with biological growth plate 22. Processor 34 then retrieves an image processing profile from image processing profile memory 36. The image processing profile corresponds to the detected plate type. Processor 34 may take the form of a microprocessor, digital signal processor, application specific integrated circuitry (ASIC), field programmable gate array (FPGA) or other integrated or discrete logic circuitry programmed or otherwise configured to provide functionality as described herein.

Using the image processing profile, processor 34 loads appropriate image analysis parameters and proceeds to process the scanned image of biological growth plate 22. In this manner, processor 34 forms an image processing device in the sense that it processes the image data obtained from biological growth plate 22. The image analysis parameters may vary with the image processing profile and detected plate type, and may specify particular parameters such as colony color, size, shape and proximity criteria for analysis of the scanned image.

For some plate types, for example, the color of surrounding nutrient media may be an indicator of high colony counts. Also, in the case of plates containing a specific carbohydrate and pH indicator, color may be an indicator of the type of organism. Adjacent objects, such as gas bubbles also may be an indicator of the type of organism. Accordingly, a variety of image processing criteria and associated parameters may be specified for various plate types. The criteria may differ according to the type of plate 22 to be analyzed, and may significantly affect colony count or other analytical results produced by biological scanner 10.

Upon selection of the appropriate image processing parameters, processor 34 processes the scanned image and produces an analytical result, such as a colony count, which is presented to a user via display 16. Processor 34 also may store the analytical result in memory, such as count data memory 38, for later retrieval from scanner 10. The data stored in count data memory 38 may be retrieved, for example, by a host computer that communicates with biological scanner 10 via a communication port 40, e.g., a universal serial bus (USB) port. The host computer may compile analytical results for a series of biological growth plates 22 presented to biological scanner 10 for analysis.

Automated selection of image processing profiles within biological scanner 10 can provide a convenient and accurate technique for selecting the appropriate image processing profile. Automated selection of image processing profiles can promote the accuracy of bacterial colony counts and other analytical procedures. In particular, automatic image processing profile selection can avoid the need for a technician to visually identify and manually enter the plate type. In this manner, plate identification errors sometimes associated with human intervention can be avoided. Consequently, the combination of a scanner 10 and a biological growth plate 22 that carries plate type indicator 28 can promote efficiency and workflow of laboratory technicians while enhancing analytical accuracy and, in the end, food safety and human health.

Figure 7:
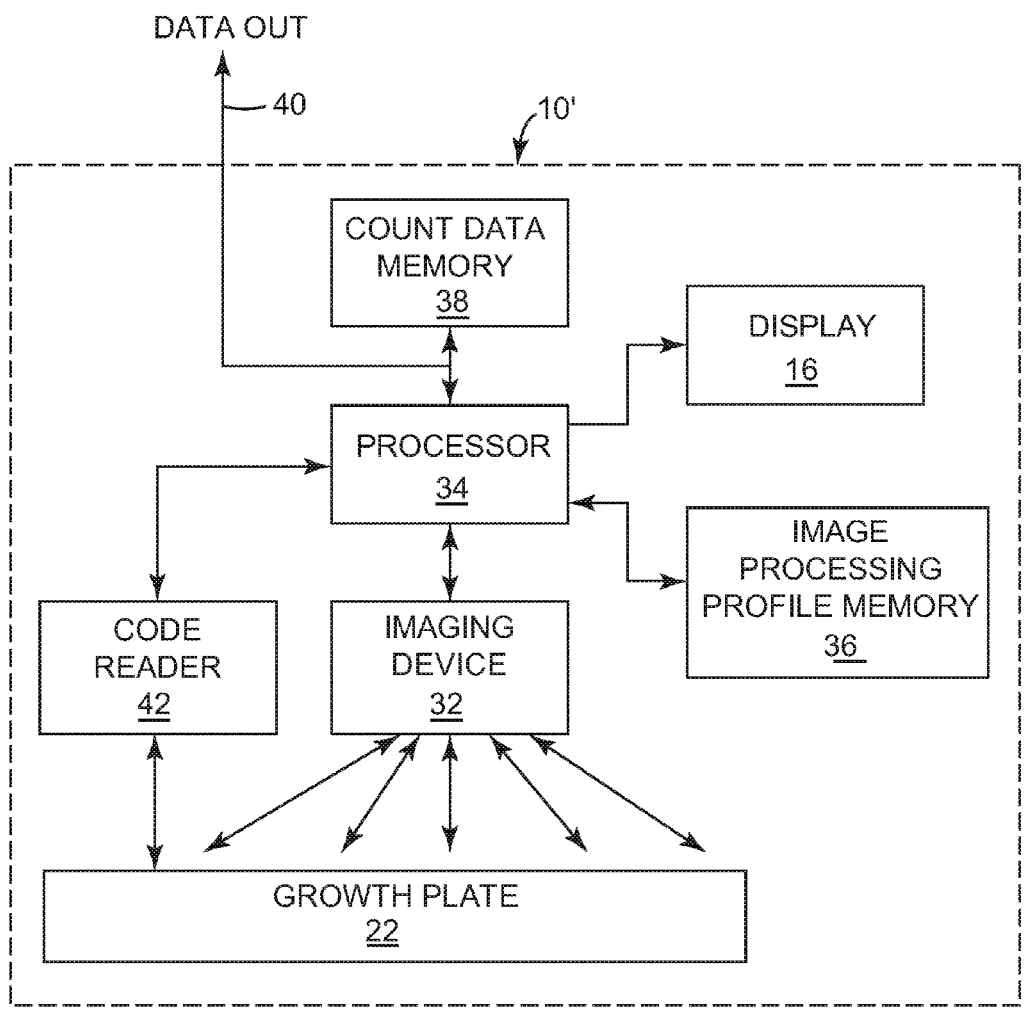
FIG. 7 is a block diagram illustrating another biological scanner configured for automated image processing profile selection.

FIG. 7 is a block diagram illustrating another biological scanner 10' configured for automated image processing profile selection. Biological scanner 10' conforms substantially to biological scanner 10 of FIG. 6, but further includes a code reader 42. Instead of extracting plate type indicator 28 from a scanned image of biological growth plate 22, code reader 42 serves as a dedicated reader to obtain plate type information. For example, depending on the form of plate type indicator 28, code reader 42 may take the form of a dedicated optical reader, bar code reader, magnetic reader, radio frequency or mechanical reader.

In each case, code reader 42 serves to identify the plate type from plate type indicator 28 and communicates the plate type to processor 34. Processor 34 then selects an image processing profile from memory 36 based on the identified plate type. Imaging device 32 scans biological growth plate 22 and provides the image date to processor 34. Processor 34 then applies the image processing parameters specified by the retrieved image processing profile to process the image and produce an analytical result such as colony count. In this manner, processor 34 applies the appropriate image processing profile on an automated basis in view of the automatically identified plate type, offering enhanced accuracy, efficiency and convenience to the user. In particular, in such an embodiment, the invention eliminates the need for the user to enter the plate type identification manually, and reduces the likelihood of analytical error due to erroneous human input.

Figure 8:
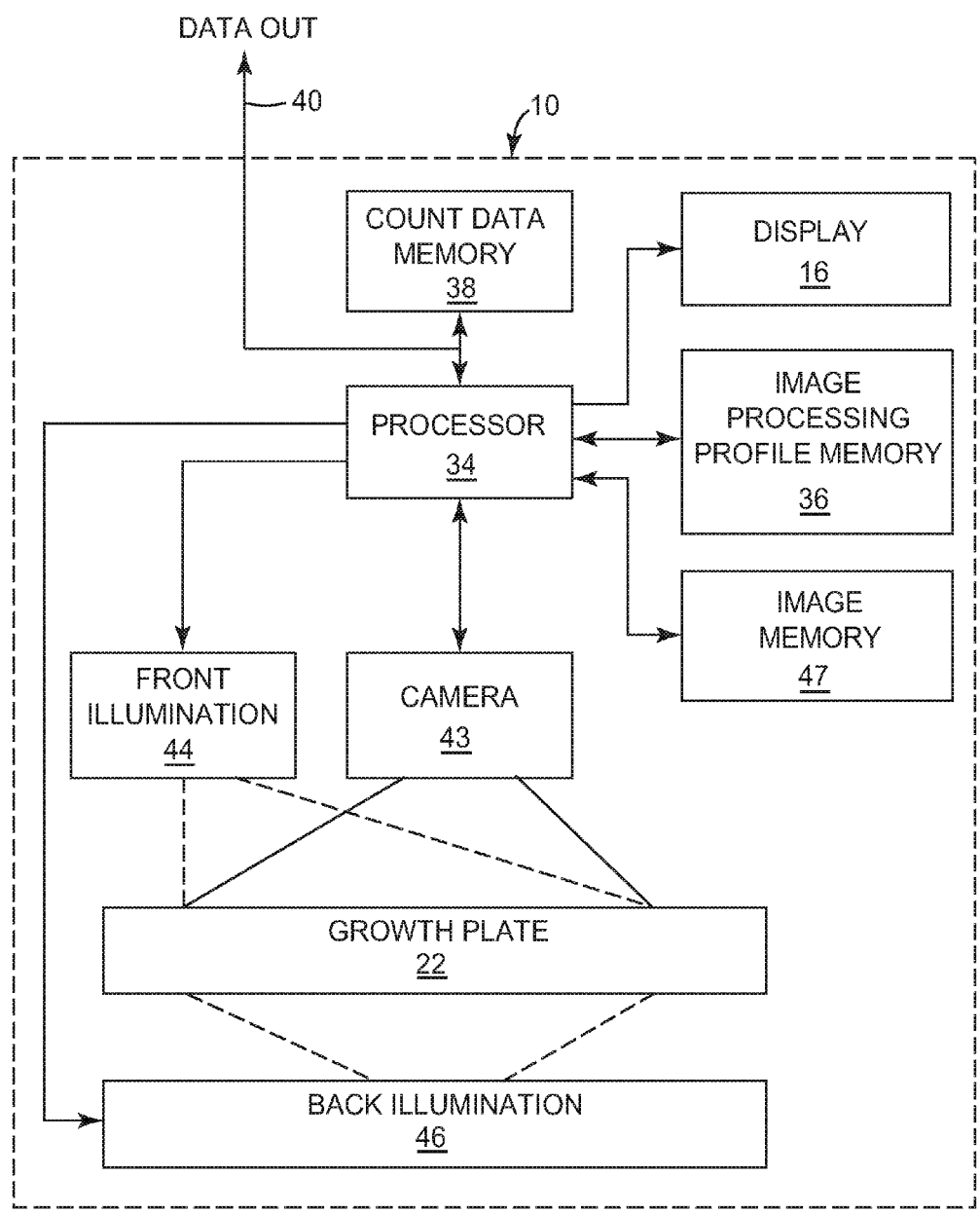
FIG. 8 is a block diagram illustrating the biological scanner of FIG. 6 in greater detail and depicting plate illumination hardware.

FIG. 8 is a block diagram illustrating biological scanner 10 of FIG. 6 in greater detail and depicting plate illumination hardware. As shown in FIG. 8, biological scanner 10 may include a front illumination system 44 and a back illumination system 46. Front illumination system 44 illuminates a front side of biological growth plate 22, and back illumination system 46 illuminates a back side of the biological growth plate. Front and bottom illumination systems 44, 46 may produce different illumination intensities, colors and durations on a selective basis. In particular, processor 34 controls front and bottom illumination systems 44, 46 to expose biological growth plate 22 to different illumination colors. Front and back illumination systems 44, 46 may incorporate LEDs as illumination sources. The LEDs can be readily controlled by processor 34 and appropriate driver circuitry to achieve desired illumination intensities and durations.

In addition, processor 34 may control camera 43 to capture images of biological growth plate 22 during illumination with the different colors. For example, processor 34 may provide coordinated control of illumination systems 44, 46 and camera 43 to capture one or more images of biological growth plate 22. Camera 43 captures one or more images of biological growth plate 22 during illumination by front illumination system 44, back illumination system 46 or both, and may store the images in an image memory 47. In some cases, processor 34 may control camera gain, resolution, aperture, exposure time or the like in response to the image capture conditions specified by the image processing profile.

Using the stored images, processor 34 performs image analysis according to the image analysis criteria specified by the image processing profile. In particular, processor 34 then may analyze the individual images or combine the multiple images to form a composite image. In some embodiments, for example, processor 34 may control illumination systems 44, 46 to capture red, green and blue images of biological growth plate 22 and analyze the images individually or as a composite multi-color image.

Some types of biological growth plates 22 may require illumination with a particular color, intensity and duration. In addition, some biological growth plates 22 may require only front or back illumination, but not both. For example, an aerobic count plate may require only front illumination as well as illumination by only a single color such as red. Also, an *E. coli*/Coliform plate may require only back illumination and a combination of red and blue illumination. Similarly, particular intensity levels and durations may be appropriate, as well as different camera gain, resolution, aperture, and exposure time. For these reasons, processor 34 may control illumination and camera conditions in response to image capture conditions specified by an image processing profile. In other words, scanner 10 can be configured to select not only image analysis criteria based on plate type, but also image capture conditions to be applied to capture the image.

To permit identification of plate type in advance of illumination, scanner 10 may apply techniques similar to those described with respect to FIGS. 6 and 7. As described with respect to FIG. 7, for example a dedicated code reader may be provided to identify plate type in advance of illumination for image capture. Upon identification of the plate type using the dedicated reader, processor 34 selects a corresponding image processing profile from image processing profile memory 36 and controls illumination according to image capture conditions specified in the image processing profile.

Alternatively, scanner 10 may be configured to apply machine vision techniques to identify the plate type from a capture image, as discussed with respect to FIG. 6. In this case, scanner 10 may apply a set of default illumination conditions to capture an initial image of biological growth plate 22, or a portion thereof, for purposes of analyzing plate type indicator 28 for plate type identification. Then, processor 34 may select a corresponding image processing profile and apply the specified image capture conditions to capture an image for analysis of biological growth.

The image processing profiles are generally described herein as specifying illumination conditions, image analysis criteria or both. However, separate profiles could be used for image capture and image analysis. For example, following plate type identification, processor 34 may access an image capture profile specifying image capture conditions such as illumination colors, intensities and durations. Then, for analysis of a captured image, processor 34 may access a separate image analysis profile specifying image analysis criteria such as color, shape, size and proximity.

Although the examples of FIGS. 6-8 refer to automated selection of image processing profiles based on plate type, the selection may be semi-automated in some embodiments. In particular, upon detection of the plate type via plate type indicator 28, processor 34 may present a preliminary plate type identification to a user via display 16. In addition, processor 34 may permit the user to either confirm or reject the automatically identified plate type before proceeding with image capture or analysis using a corresponding image processing profile. The user may confirm or reject a preliminary plate type identification, for example, by actuating a pointing device or depressing regions of a touch screen. If the user believes that the automatically detected plate type identification is in error, processor 34 may permit the user to change the plate type identification.

Figure 9:
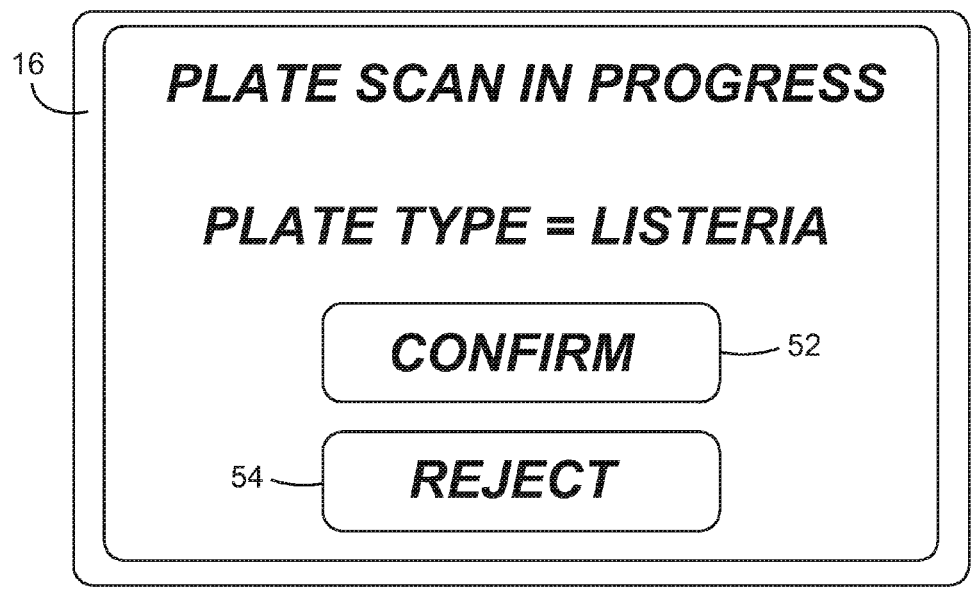
FIG. 9 illustrates sample display content produced on a display by a biological scanner upon plate type detection.

FIG. 9 is a sample display content produced on display 16 by biological scanner 10 upon plate type detection. As shown in FIG. 9, display 16 presents a preliminary plate type identification, i.e., a plate type identification automatically made by processor 34. In the example of FIG. 9, display 16 indicates that the "PLATE TYPE=LISTERIA." In addition, display 16 presents two touch screen regions 52, 54 that accept user input to indicate whether the preliminary plate type identification is confirmed or rejected, respectively, by the user.

Figure 10:
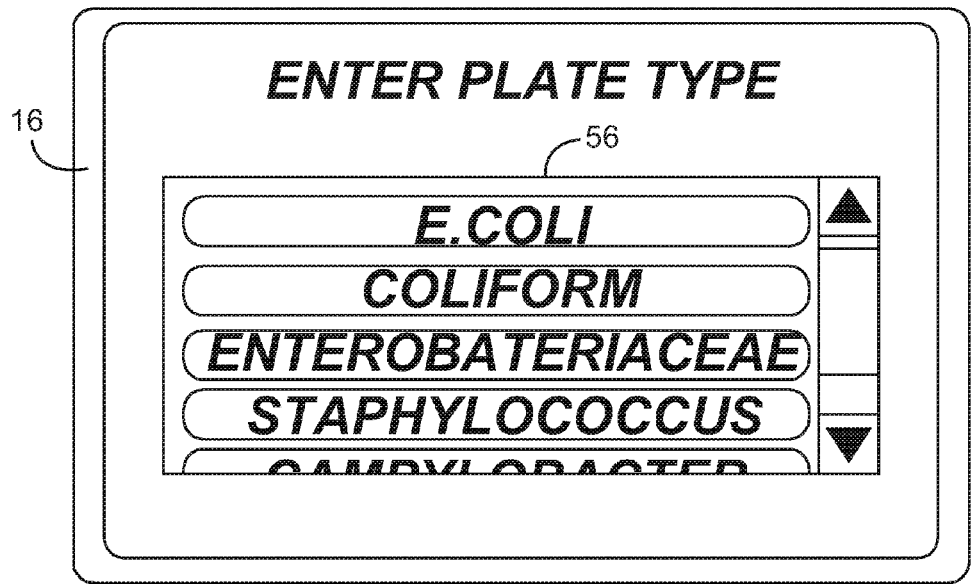
FIG. 10 illustrates sample display content produced on a display by a biological scanner 10 upon rejection of an automated plate type detection by a user.

FIG. 10 is sample content produced by display 16 of biological scanner 10 upon rejection of the automated plate type detection by the user. For example, in the event the user rejects a preliminary plate type identification as shown in FIG. 9, processor 34 may drive display 16 to present an "ENTER PLATE TYPE" dialog by which the user may choose the correct plate type identification, as shown in FIG. 10. Display 16 may present a vertical scroll bar menu 56 that permits the user to choose an alternative plate type identification, e.g., by depressing an appropriate touch screen region. Upon selection of an alternative plate type identification, processor 34 may select an alternative image processing profile containing, for example, image capture conditions, image analysis criteria, or both.

Figure 11:
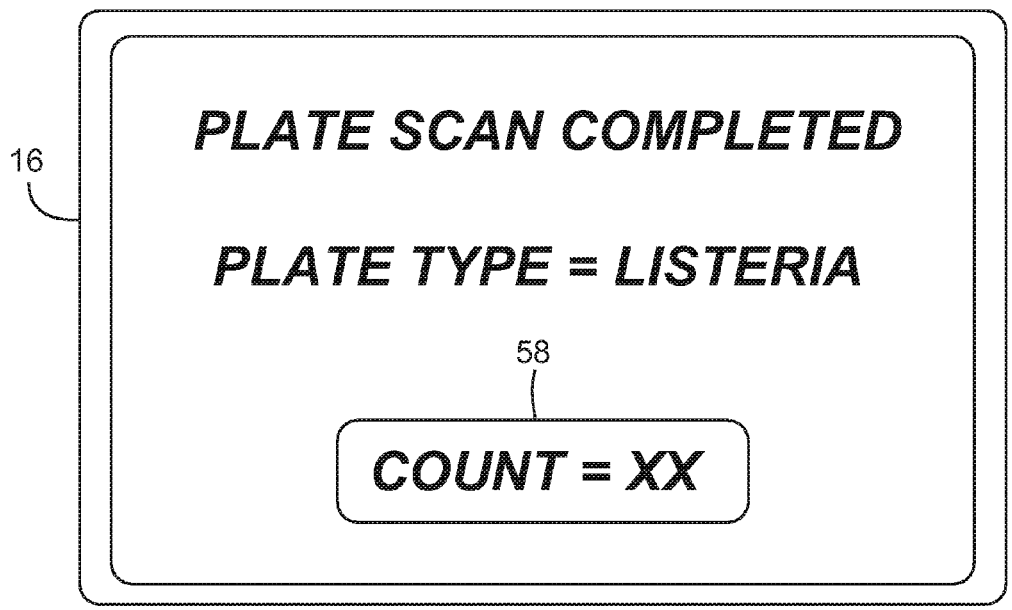
FIG. 11 illustrates sample display content produced on a display by a biological scanner upon determination of a colony count.

FIG. 11 is sample content produced by display 16 of biological scanner 10 upon determination of a colony count. As shown in FIG. 11, processor 34 may drive display 16 to present a message that the "PLATE SCAN COMPLETED" and identify the plate type ("PLATE TYPE=LISTERIA"). In addition, upon completion of the analysis of biological growth plate 22, processor 34 drives display 16 to present a count 58 ("COUNT=XX"). Display 16 may present other types of analytical results as well.

Figure 12:
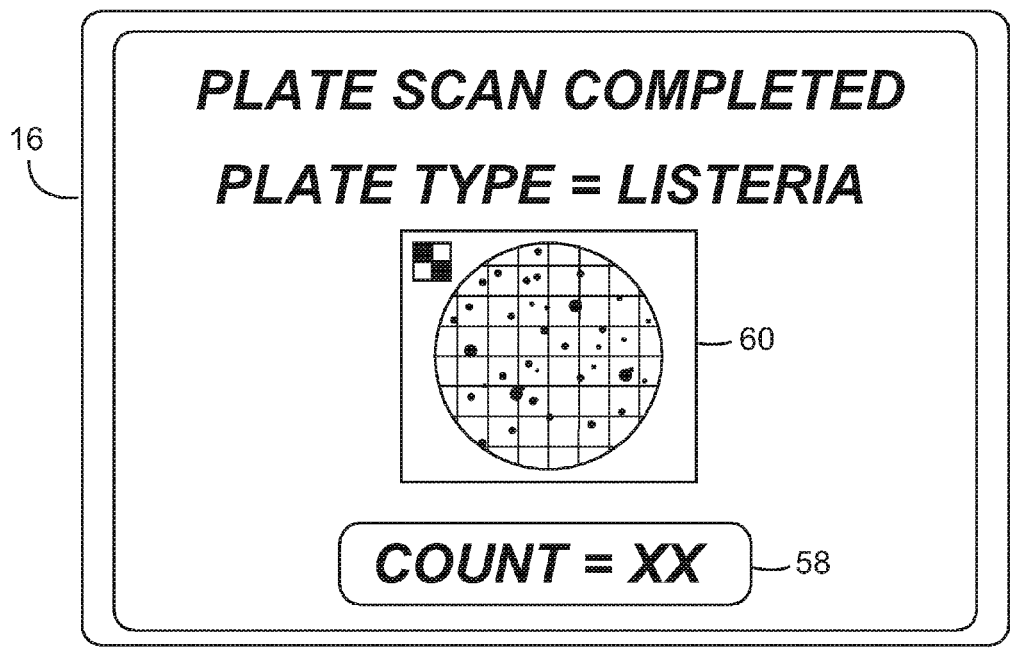
FIG. 12 illustrates sample display content produced on a display by a biological scanner upon determination of a colony count and including an image of a scanned plate.

FIG. 12 is sample content produced by display 16 of biological scanner 10 upon determination of a colony count and including an image of a scanned plate. In the example of FIG. 12, display 16 presents information similar to that shown in FIG. 11, but further includes a representation 60 of the actual image scanned by biological scanner 10 from the surface of biological growth plate 22. In this manner, the user can view both the analytical result, such as count 58, and a representation 60 of the scanned image. In some embodiments, image representation 60 may present a sufficient amount of detail to permit the user to verify the automatically determined count. In other embodiments, image representation 60 may be a lower resolution representation.

Figure 13:
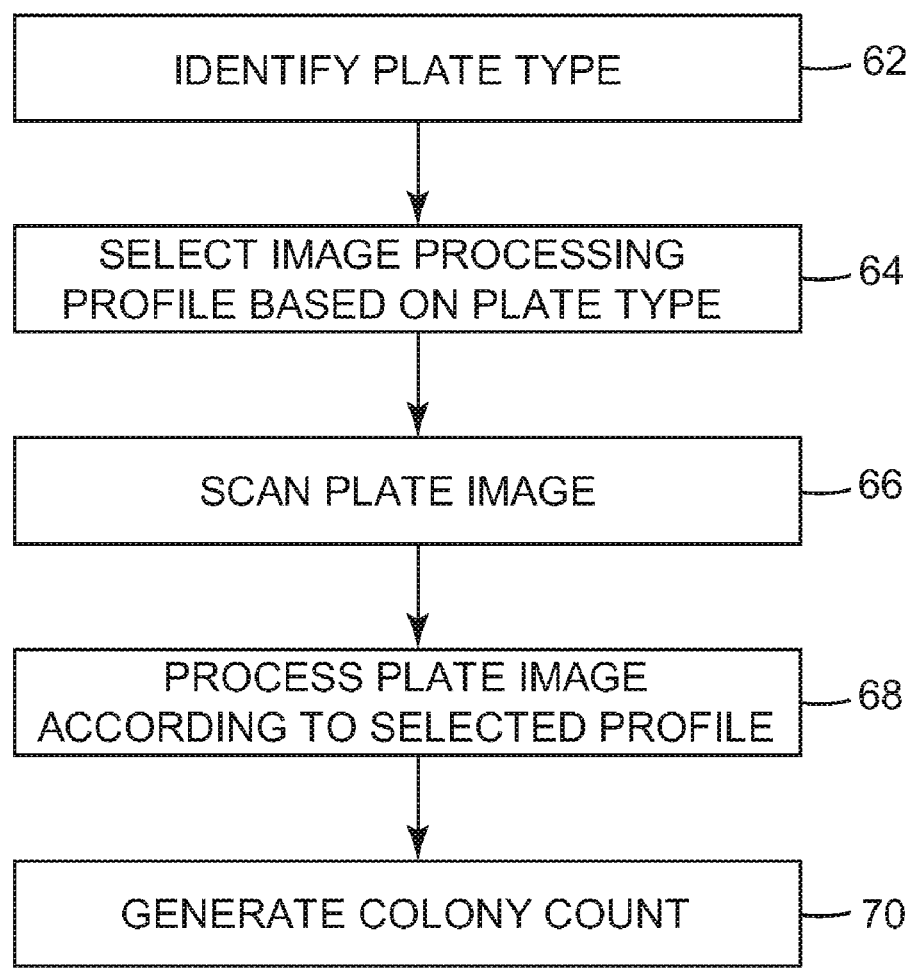
FIG. 13 is a flow diagram illustrating a process for image processing profile selection in biological scanner.

FIG. 13 is a flow diagram illustrating a process for image processing profile selection in biological scanner 10. As shown in FIG. 13, the process may involve identifying a plate type (62) for a biological growth plate 22 presented to scanner 10. The process may further involve selection of an image processing profile based on the plate type (64), either before or after scanning a plate image (66). If the image processing profile specifies image capture conditions, the image processing profile should be selected prior to scanning the plate image so that illumination conditions, camera properties or both may be controlled. Using image analysis criteria specified by the selected image processing profile, the process further involves processing the plate image to produce an analytical result (68). In particular, the process may generate a bacterial colony count (70). In the example of FIG. 13, the plate type is identified before the plate image is scanned.

Figure 14:
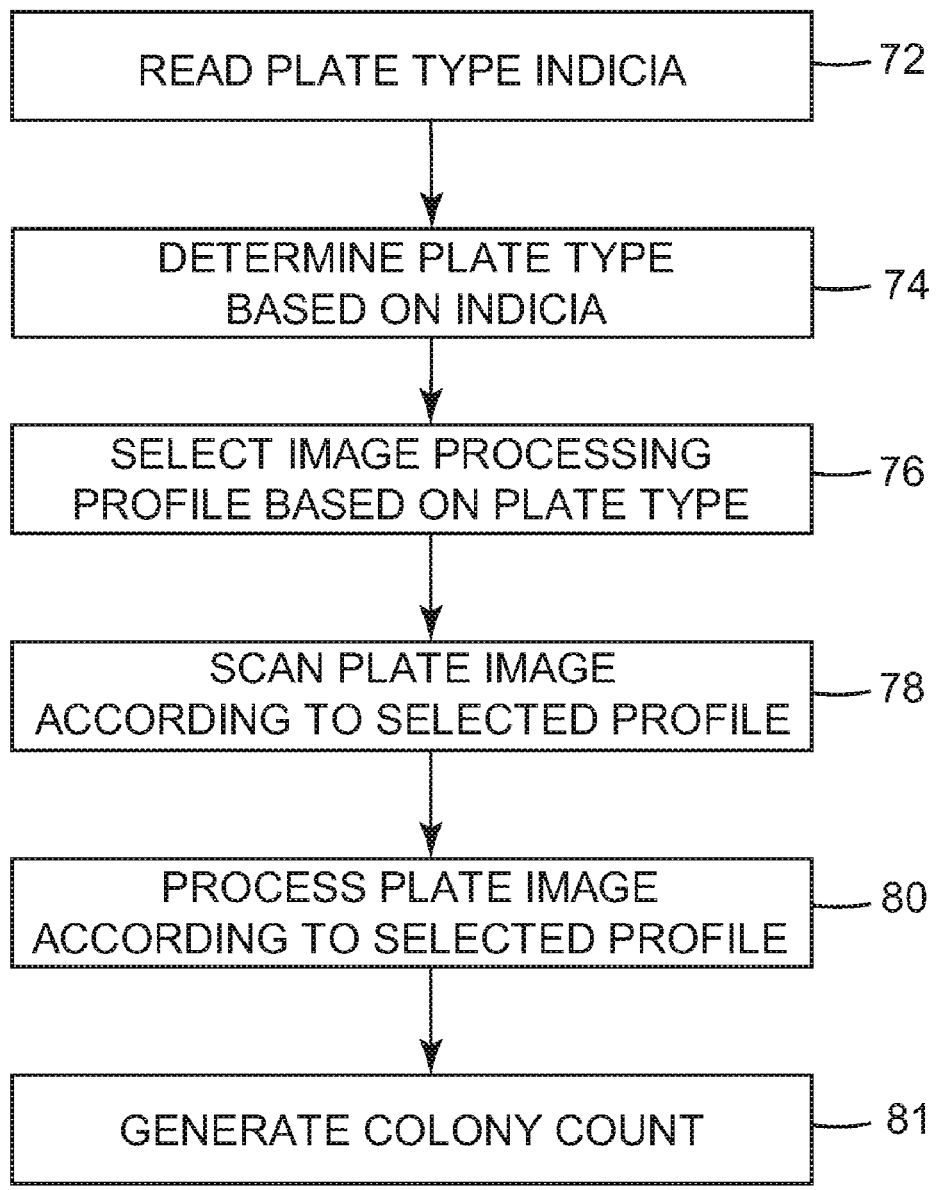
FIG. 14 is a flow diagram illustrating a process for image processing profile selection in a biological scanner involving detection of a plate type indicator.

FIG. 14 is a flow diagram illustrating a process for image processing profile selection in a biological scanner involving detection of a plate type indicator. As shown in FIG. 14, the process involves reading the plate type indicator carried by a biological growth plate (72), e.g., with a dedicate plate type indicator reader such as an optical reader, bar code reader, magnetic reader, radio frequency reader, mechanical reader or the like. Upon determination of the plate type based on the plate type indicator (74), the process involves selecting an image processing profile based on the detected plate type (76). In addition, the process involves scanning an image of the biological growth plate (78), and processing the plate image according to parameters specified by the selected image processing profile (80). The process then produces an analytical result such as a colony count (81).

Figure 15:
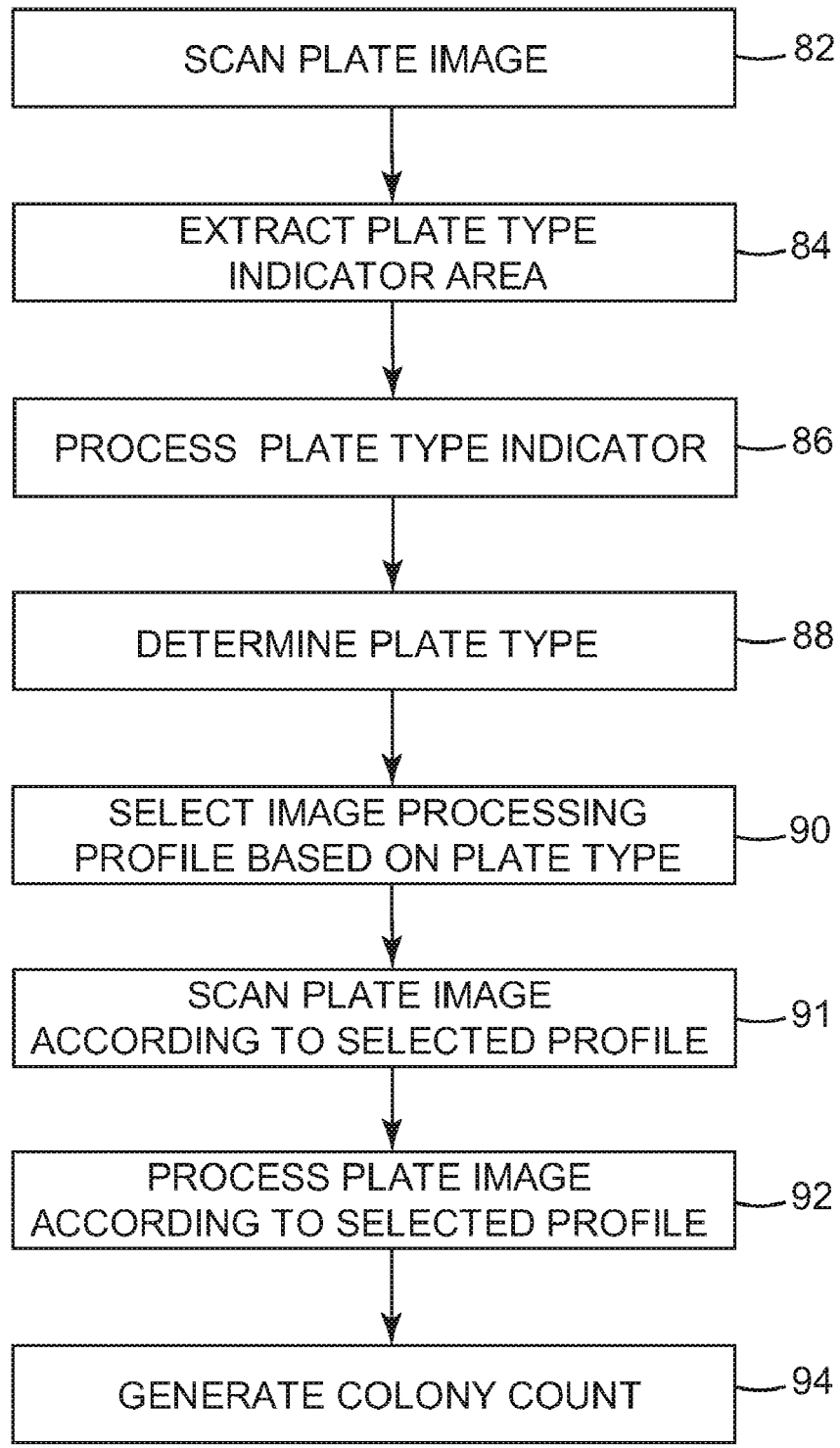
FIG. 15 is a flow diagram illustrating a process for image processing profile selection in a biological scanner involving extraction of a plate type indicator from a scanned plate image.

FIG. 15 is a flow diagram illustrating a process for image processing profile selection in a biological scanner involving extraction of plate type indicator from a scanned plate image. As shown in FIG. 15, the process involves scanning an image of a biological growth plate (82), and extracting a plate type indicator area from the scanned image (84). The process further involves processing the extracted plate type indicator area (86) to determine the plate type (88). Upon determination of the plate type based on the plate type indicator (88), the process involves selecting an image processing profile based on the detected plate type (90). The process then may involve scanning the plate again (91), e.g., using image capture conditions specified by the selected image processing profile, and processing the plate image according to image analysis criteria specified by the selected image processing profile (92). The process then produces an analytical result such as a colony count (94).

Figure 16:
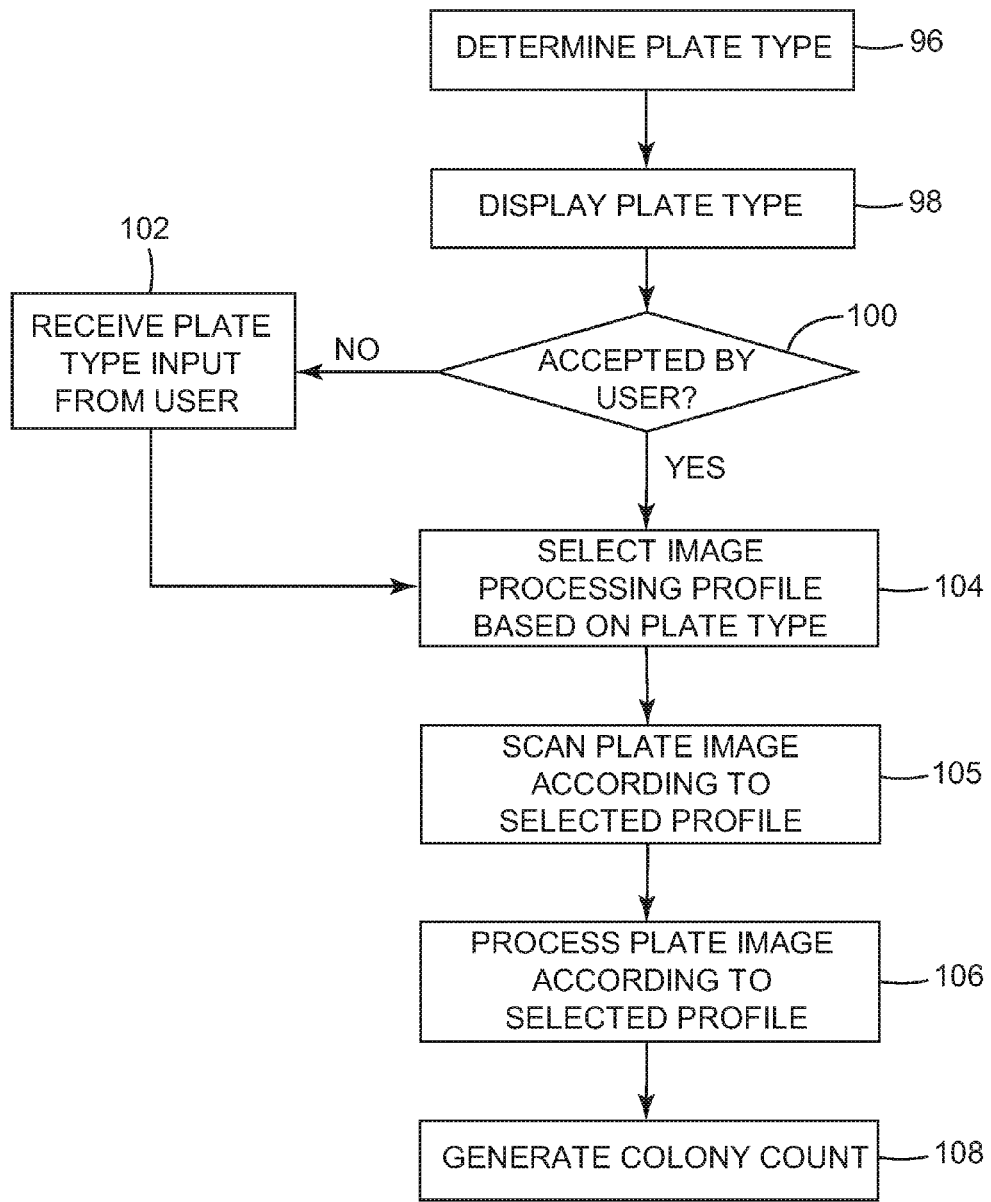
FIG. 16 is a flow diagram illustrating a process that permits a user to override an automatic plate type identification by a biological scanner.

FIG. 16 is a flow diagram illustrating a process that permits a user to override an automatic plate type identification by a biological scanner. As shown in FIG. 16, the process involves automatically determining a plate type associated with a biological growth plate 22 (96), and presenting the determined plate type to a user via display 16 (98). The process further involves accepting user input to accept or reject the automatically determined plate type (100), e.g., via touch screen input. If the plate type is not accepted by the user, the process involves accepting user input to receive a plate type from the user (102). Upon entry of a plate type by the user (102) or acceptance of an automatically determined plate type (100), the process involves selection of an image processing profile based on the plate type (104). Using the selected image processing profile, the process scans a plate image (105), processes the plate image (106) and generates a colony count (108) or some other desired analytical result.

In operation, processor 34 executes instructions that may be stored on a computer-readable medium to carry out the processes described herein. The computer-readable medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like.

Various modifications may be made without departing from the spirit and scope of the invention. These and other embodiments are within the scope of the following claims.

The invention claimed is:

1. A method, comprising:
   providing a biological scanner and a biological growth plate that includes a plate type indicator, wherein the biological scanner includes an imaging device, a processor, and an image processing profile memory;
   scanning the plate type indicator with the scanner to detect a plate type associated with the biological growth plate;
   having the processor retrieve an image processing profile corresponding to the detected plate type;
   having the processor use the plate type indicator to verify the suitability of the biological growth plate for use in the biological scanner.

2. The method of claim 1, wherein the suitability of the biological growth plate is verified using plate type indicator information selected from the group consisting of a particular manufacturer, a lot number, an expiration date, and a security authorization.

3. The method of claim 1, further comprising:
   rejecting the biological growth plate according to information in the plate type indicator.

4. A method, comprising:
   providing a biological scanner and a biological growth plate that includes a plate type indicator, wherein the biological scanner includes an imaging device, a processor, and an image processing profile memory;
   scanning the plate type indicator with the scanner to detect a plate type associated with the biological growth plate;
   processing the plate type indicator with the processor to unlock the biological scanner for operation.

* * * * *